(12) United States Patent
Schultz et al.

(10) Patent No.: US 7,939,339 B2
(45) Date of Patent: May 10, 2011

(54) ARRANGEMENT FOR FLUORESCENCE AMPLIFICATION

(75) Inventors: Niko Schultz, Mainz (DE); Samuel D. Conzone, Mainz (DE); Otmar Becker, Langen (DE); Dan Haines, Lake Ariel, PA (US); Edgar Pawlowski, Stadecken Elsheim (DE); Volker Scheumann, Mainz (DE)

(73) Assignee: Schott AG, Mainz (DE)

( * ) Notice: Subject to any disclaimer, the term of this patent is extended or adjusted under 35 U.S.C. 154(b) by 1185 days.

(21) Appl. No.: 11/082,518

(22) Filed: Mar. 17, 2005

(65) Prior Publication Data
US 2005/0244860 A1 Nov. 3, 2005

(30) Foreign Application Priority Data
Mar. 17, 2004 (DE) .................. 10 2004 013 388

(51) Int. Cl.
*G01N 21/00* (2006.01)
*G01N 33/551* (2006.01)
*G01N 33/552* (2006.01)
*G01N 33/553* (2006.01)
*G01N 21/64* (2006.01)
*H04B 1/02* (2006.01)

(52) U.S. Cl. ........ 436/164; 436/524; 436/535; 436/527; 252/520.22

(58) Field of Classification Search .............. None
See application file for complete search history.

(56) References Cited

U.S. PATENT DOCUMENTS

| | | | | |
|---|---|---|---|---|
| 4,882,617 A | * | 11/1989 | Vriens | 348/779 |
| 5,494,829 A | * | 2/1996 | Sandstrom et al. | 436/518 |
| 6,208,423 B1 | | 3/2001 | Voipio et al. | |
| 7,195,872 B2 | * | 3/2007 | Agrawal et al. | 435/6 |
| 2003/0148401 A1 | * | 8/2003 | Agrawal et al. | 435/7.9 |

FOREIGN PATENT DOCUMENTS

DE 199 27 484 12/1999

(Continued)

OTHER PUBLICATIONS

U.S.P.T.O., CY3 trademark, 2009. Retrieved from: http://tess2.uspto.gov/bin/showfield?f=doc&state=4002:qe87vj.3.1.*

(Continued)

*Primary Examiner* — Mark Staples
(74) *Attorney, Agent, or Firm* — Ohlandt, Greeley, Ruggiero & Perle, LLP

(57) ABSTRACT

The invention relates to an arrangement for fluorescence amplification including a substrate, a fluorescence amplifier coating applied to the substrate, and a thin fluorescencable material which lies on the coating and emits light with the emission wavelength $\lambda_E$ when it is exposed to excitation light of an excitation wavelength $\lambda_A$. The fluorescence amplifier coating includes an interference layer system of high-index and low-index dielectric layers, which reflects at least the excitation light. What is crucial for the design of the coating is that the fluorescencable material applied to the coating is arranged on the surface of the coating in the region of the maximum of the electric field amplitude of the standing wave with the excitation wavelength $\lambda_A$, which is formed during exposure to the excitation light.

43 Claims, 5 Drawing Sheets

FOREIGN PATENT DOCUMENTS

| | | |
|---|---|---|
| DE | 100 52 165 | 5/2002 |
| EP | 1 591 773 B1 * | 8/2008 |
| GB | 2 227 089 | 7/1990 |
| WO | WO 91/18292 | 11/1991 |
| WO | WO 98/53304 | 11/1998 |
| WO | WO 00/23793 | 4/2000 |
| WO | WO 02/48691 | 6/2002 |

OTHER PUBLICATIONS

U.S.P.T.O., CY5 trademark, 2009. Retrieved from: http://tess2.uspto.gov/bin/showfield?f=doc&state=4002:qe87vj.2.1.*

Lukosz, Light emission by multipole sources in thin layers. I. Radiation patterns of electric and magnetic dipoles, J. Opt. Soc. Am./vol. 71, No. 6/Jun. 1981, pp. 744-754.*

Lakowicz et al., Effects of Silver Island Films on the Luminescent Intensity and Decay Times of Lanthanide Chelates, Journal of Fluorescence, vol. 12, Nos. 3/4, Dec. 2002 (q 2002) pp. 431-437.*

Fluorescence spectral properties of cyanine dye-labeled DNA oligomers on surfaces coated with silver particles, Malicka et al., Analytical Biochemistry, 2003.

* cited by examiner

ARRANGEMENT FOR FLUORESCENCE AMPLIFICATION

CROSS-REFERENCES TO RELATED APPLICATIONS

The present application is claiming priority of German Patent Application No. 10 2004 013388.3-52, filed on Mar. 17, 2004, the content of which is herein incorporated by reference.

BACKGROUND OF THE INVENTION

1. Field of the Invention

The invention relates to a substrate having a coating, in particular a dielectric coating, which substantially amplifies the fluorescent excitation of a material lying on this coated substrate. The invention also relates in particular to a sample carrier which is provided with a coating and amplifies the fluorescent excitation of a sample and therefore the fluorescent light signal to be detected, and which substantially improves the signal-to-noise ratio during the fluorescence measurement.

2. Description of Related Art

Fluorescence microscopy is a conventional technology, which is employed particularly in the field of molecular biology. It is used to analyze biological materials, for example nucleic acids (DNA, RNA) and proteins (enzymes etc.). The substances to be studied are labeled with fluorescent dyes and thus made visible in a fluorescence scanner or fluorescence microscope.

Particularly in the field of biochip technology, fluorescence spectroscopy is very important for the analysis of so-called microarrays. The DNA array technique is based, for example, on the hybridization of nucleic acids (Watson Crick base pairing). In this case, two complementary nucleic acid single strands combine via a hydrogen bridging bonds between their hydrophobic purine and pyrimidine bases, in order to minimize the water contact. It was Ed Southern who first applied the principle of using labeled nucleic acids to analyze other nucleic acids (Southern Blot).

Biochips typically consist of an organic film applied to a glass substrate, on which single-stranded DNA material has been applied in the form of points (about 100 to 150 μm diameter). Successful binding of the single-stranded DNA to be analyzed, which is provided with a fluorescent dye such as cyanine dyes, including Cy3 dyes and Cy5 dyes, to the single-stranded DNA applied in the form of points on the organic film can be detected by a fluorescent DNA dot. Instead of complete DNA, it is also possible to analyze short-chained molecules (oligos).

A high detection sensitivity is in any event a necessary prerequisite for the successful use of biochips as a responsive sensor system. This detection sensitivity is essentially determined by the strength of the signal to be detected and by the signal-to-noise ratio. Sources of perturbing background signals are, for example, autofluorescence of the substrate or impurities, or of the optical components lying in the excitation light, as well as intrinsic noise in the detector. The autofluorescence of the substrate or optical components can be substantially restricted by using non-fluorescent or low-fluorescence materials. Other possibilities for the elimination of perturbing noise signals during the measurement are offered by pulsed or modulated excitation.

There are furthermore solution approaches which relate to improving the substrates or sample carriers. For example, U.S. Pat. No. 5,552,272 proposes to provide a substrate with an antireflection layer which suppresses reflection of the excitation light with a particular wavelength, and therefore reduces the noise signal. According to U.S. Pat. No. 5,552,272, this antireflection layer has no effect on the generation of the fluorescent signal, and it is possible to achieve a stronger contrast between the signal and the noise. In this case, the maximum achievable signal-to-noise ratio $SNR_{max}$ is limited to $SNR_{max} = S^{0.5}$, where S is the strength of the fluorescent signal.

With a view to further improving the fluorescence excitation and the fluorescent emission detection, and therefore a higher measurement sensitivity, WO 98/53304 discloses a sample carrier consisting of a substrate with a reflective metal surface and a transparent dielectric layer on top. The transparent dielectric layer has a thickness such that the optical path length from the layer surface to the reflective surface of the substrate corresponds to an odd multiple of $\lambda/4$, $\lambda$ being the wavelength of the excitation light. The thickness of the transparent layer is therefore determined by the wavelength of the excitation light, the refractive index n of the layer material and the angle of incidence of the beam. With such dimensioning of the dielectric layer and arrangement on a reflective metal surface, a maximum in the electric field amplitude due to the constructive superposition of the incident and reflected excitation light, and the resultant standing wave of the excitation light and the reflected excitation light of wavelength $\lambda$, is formed at the layer surface of the dielectric layer.

The reflective metal surface is obtained by the substrate itself being a metal, or being coated with a metal, and it is primarily used for reflecting the excitation light. Such reflective metals are preferably aluminum, silver, gold or rhodium, which are suitable for a wide spectrum of the excitation light. The transparent dielectric layer, on which the sample directly lies, acts as a kind of spacer layer from the reflective metal surface and makes it possible to position the sample in the region of a maximum of the electric field of the excitation beam. The sample can therefore be arranged in the maximum intensity region of the excitation and the fluorescence can be increased. The use of this sample carrier, however, is on the one hand restricted to a particular excitation wavelength (defined by the thickness of the spacer layer) and on the other hand limited by the susceptibility of the metal layers to oxidation.

U.S. Pat. No. 6,552,794 B2 discloses an optical detection method with improved measurement sensitivity having a substrate, provided with a reflective layer, as the sample carrier which reflects the fluorescent light emitted in the direction of the substrate by the sample, and having an optimized optical detection arrangement which can record both the fluorescent light emitted in its direction and the emitted fluorescent light reflected by the layer. With ideal reflection of the emitted fluorescent radiation, the measurement accuracy can then be improved by the maximum factor of 2. A substantial disadvantage of this arrangement is that it does not prevent the substrate from being excited and fluorescing as well, and thereby detrimentally affecting the measurement. The theoretical increase in the fluorescence is furthermore limited to a factor of 2.

The requirements for fluorescence detection have continued to increase, especially in the field of biochips. In most cases, it is not enough merely to establish that there is fluorescence, but it is also necessary to determine the intensity very accurately for comparative analysis with other biochips. The more accurate the measurements are, the more accurate the analysis can be.

BRIEF SUMMARY OF THE INVENTION

It is therefore an object of the invention to further improve the excitation and/or detection of fluorescence, as well as the signal-to-noise ratio in fluorescence measurements.

It is also an object of the invention to make the excitation and/or detection of fluorescence more versatile.

The object is achieved by an arrangement for fluorescence amplification which consists of a substrate, a fluorescence amplifier coating, in particular a dielectric coating, applied to the substrate, and a thin fluorescent material which lies on the coating and emits light in the emission wavelength range $\lambda_E$ when it is exposed to excitation light of an excitation wavelength $\lambda_A$, or which comprises such a substrate with a fluorescence amplifier coating. The fluorescence amplifier coating comprises an interference layer system of high-index and low-index dielectric layers, which reflects at least the excitation light.

What is essential is that the design of the interference layer system furthermore allows vertical arrangement of the fluorescent material applied to the coating, in the region of the maximum of the electric field amplitude, and in particular in the region of the maximum of the square of the electric field amplitude, of the standing wave with the excitation wavelength $\lambda_A$, which is formed during exposure to the excitation light.

The term "vertical arrangement" in the context of the invention means arrangement along a direction perpendicular to the surface of the interference layer system.

Besides the purely reflective property of the design, a second property is therefore quite essential: in the region of the surface of the interference system, the incident and reflected excitation light of the wavelength $\lambda_A$ must be constructively superposed so that a maximum of the electric field amplitude is formed there. In the ideal case, the constructive interference doubles the field strength at the surface, which leads to local quadrupling of the light intensity since this scales physically with the square of the field strength. Here, the term region of the surface means in particular the region in which the fluorescent material is or will be arranged. It is preferably a region in the vertical direction starting at the surface of the interference layer system up to a distance of one fourth of the wavelength above the surface.

According to the invention, therefore, the interference layer system of the arrangement preferably leads to a phase relation of the excitation light such that constructive interference takes place between the incident and reflected excitation light immediately on the surface or in the region of one half of the wavelength, preferably one fourth of the wavelength above the surface, and a maximum electric field is formed in the region of the fluorescing material which is or can be applied.

In order to achieve an amplifying effect overall, the layer thickness of the fluorescent material should preferably not exceed one half of the wavelength, so that amplifying and attenuating effects are not averaged out.

An amplifying effect can also be achieved if the maximum of the electric field amplitude does not lie at or above the surface of the interference layer, but lies slightly below the surface. This is so, in particular, when the maximum lies less than one fourth of the wavelength below the surface.

Particularly preferably, the interference layer system is furthermore designed so that the phase relation of the excitation light remains constant along the surface in the region of the fluorescent material. This prevents intensity minima from occurring in addition to intensity maxima along the surface in the region of the fluorescent material. In order to guarantee a constant phase relation, the interference layer system may in particular [lacuna] along the surface in the region of the fluorescent material which is present or can be applied [lacuna]

The fluorescent material is not in this case necessarily a component of the arrangement. Instead, the fluorescent material may also be applied subsequently to the interference layer system, for example for suitable studies. The invention therefore also relates to an arrangement for fluorescence amplification having a substrate and a fluorescence amplifier coating applied to the substrate, with a surface for the arrangement of fluorescent material which emits light of an emission wavelength in the range $\lambda_E$ when it is exposed to excitation light of an excitation wavelength $\lambda_A$, the fluorescence amplifier coating comprising an interference layer system of high-index and low-index dielectric layers which reflects at least the excitation light, and the surface of the fluorescence amplifier coating being arranged in the region of the maximum of the electric field amplitude, or in particular the square of this amplitude, of the standing wave with the excitation wavelength $\lambda_A$ which is formed during exposure to the excitation light. In this arrangement as well, whenever it is applied the fluorescent material is therefore located in the region of the maximum of the electric field amplitude, and in particular in the region of the light intensity of the excitation light which is proportional to the square of the amplitude.

In particular, it is then preferable for the interference layer system to be configured so that the surface of the coating is arranged slightly below the spatial maximum of the light intensity of the excitation light, so that the maximum of the light intensity then lies within the fluorescent coating or layer which can be applied. To this end, for example, the surface of the fluorescent coating may lie in the region of up to at most 50 nanometers below the maximum of the square of the field amplitude, so that the fluorescent coatings which are thicker, in particular two times as thick as this distance, can be excited particularly effectively in fluorescence.

The excitation wavelength $\lambda_A$ may in this case be a narrow spectral range, as is found in commercial spectrometers where it is defined by bandpass filters in front of a white light source.

The fluorescence amplifier coating has two properties, fulfills two functions: (i) the formation of a standing wave at the excitation wavelength $\lambda_A$ by high reflection, or design as a reflective coating, and (ii) as design-related provision of a high field strength at the surface, or in the region of the surface wherever the fluorescent material is or will be arranged, owing to a phase relation of incident and reflected excitation light dictated by the choice of the sequence and layer thickness of the individual layers of the interference layer system.

Condition (ii) also corresponds to a design-related vertical arrangement of the fluorescent material in the region of the standing wave, which has a maximum E-field amplitude of the excitation light, so that maximum fluorescence excitation is possible. A substantial amplification of the fluorescence can therefore be achieved by straightforward means.

For an optimal fluorescence enhancing effect, it is preferable for the maximum of the electric field amplitude of the standing wave to lie in the middle of the layer thickness of the fluorescent material, or for the material to be so thin that the maximum of the electric field amplitude of the standing wave lies at the interface between the coating and the fluorescent material. The thickness of the fluorescent material and the design configuration of the fluorescence amplifier coating therefore have to be tailored to each other.

For example, the order of magnitude of the excitation wavelength $\lambda_A$ then gives an expedient possible order of magnitude for the thickness of the fluorescent material. For a design of the coating such that the maximum of the electric field amplitude of the standing wave lies at the interface between the coating and the fluorescent material, the fluorescent material should have a thickness which is thin compared with the excitation wavelength $\lambda_A$, preferably less than half and particularly preferably less than one fourth of the excitation wavelength $\lambda_A$.

The simplest design with the greatest effect is achieved with interference layer systems of alternating high-index layers (H) and low-index layers (L), each of which has an optical layer thickness that corresponds to one fourth of the excitation wavelength $\lambda_A$. Such a design may start with a high-index or low-index layer on the substrate surface, and must have a low-index layer at the interface with the fluorescent material. Typical designs have the form substrate/(HL)$^n$/fluorescent material or substrate/L/(HL)$^n$/fluorescent material with n>1, the reflection of the excitation light being increased and the effect of the coating therefore being improved when n=4, and in particular n=8.

Such designs reflect the excitation light and form a standing wave with a maximum of the E-field amplitude at the surface. Designs with higher reflection then have a higher electric field amplitude E of the standing wave than less reflective designs. The fluorescence excitation increases proportionally to $E^2$. Since a maximum of the electric field amplitude of the standing wave is formed at the surface of such designs, maximum excitation of the correspondingly thin fluorescent material lying on this surface takes place.

Similar results may, for example, also be achieved with alternating designs, for example with interference layer systems as described above, which furthermore have doubled high-index layers (H) and/or doubled low-index layers (L). These so-called half-lambda layers may lie at any place in a design with alternating high-index and low-index layers.

There are also a multiplicity of other designs which fall within the scope of the invention and which likewise exhibit a high electric field amplitude at the excitation wavelength on the surface of the interference layer system or inside the fluorescent material, and good reflection of the excitation light. Also viable are interference layer systems whose individual layers deviate from the optical layer thickness of one fourth of the wavelength of the excitation light and/or which consist of more than two materials. For an equivalent fluorescent amplification, however, these generally have a more complicated or expensive design.

Other suitable embodiments of the fluorescence amplifier coatings described above, especially for fluorescence measuring arrangements, are optical filter designs which predominantly reflect light in the excitation wavelength range $\lambda_A-20$ nm$\leq\lambda_A\leq\lambda_A+20$ nm, preferably $\lambda_A-10$ nm$\leq\lambda_A\leq\lambda_A+10$ nm, and whose reflectivity in this range is more than 50%, preferably more than 80%.

Arrangements in which the interference layer system is an optical filter that reflects light at least in the range of the excitation wavelength $\lambda_A$ and transmits in the range of the emission wavelength $\lambda_E$ are likewise possible suitable and preferred embodiments, especially when the fluorescence is measured or used not in reflection but in transmission through the substrate. This, however, presupposes that the substrate is then also transmissive for the emission light. Possible applications are illuminating objects which are excited from the inside and are intended to emit fluorescent light outward. Such an illuminating object having a layer system according to the invention may, in particular, be a fluorescent tube. With the invention, the fluorescent dye can thereby be utilized very effectively and used merely in very thin layers to save material. Other applications are measuring arrangements in which the fluorescence is intended to be measured in transmission, for example in quality control. This illustrates the substantially more versatile use of the arrangement according to the invention, compared with known solutions as disclosed for instance in the documents WO 98/53304 and U.S. Pat. No. 6,552,794 b2.

Often, microarrays are excited simultaneously or in close succession with two different wavelengths. Another substantial advantage of the arrangement according to the invention is the opportunity to adapt the interference layer system to such requirements, and to configure it with a suitable design such that it simultaneously has equally large electric field amplitudes at two or more discrete excitation wavelengths, so that amplified fluorescence occurs at least at two wavelengths. An arrangement according to the invention can therefore be used for fluorescence excitations at a plurality of wavelengths. Such simultaneous adaptation to two or more wavelengths is not possible with the known metal/dielectric coatings (for instance according to WO 98/53304).

For example, the fluorescence amplifier coating may preferably be configured so that it amplifies excitation light with an excitation wavelength around 535 nanometers and around 635 nanometers in the region of the fluorescent material, i.e. in the region of the surface wherever the fluorescent material is or will be arranged in a vertical direction. These wavelengths are commonly used for fluorescence measurements on organic, in particular biological samples. In particular, the interference layer system may be configured so that it amplifies at these two wavelengths.

Another advantage is that besides the one or more maxima of the square of the field amplitude, one or more pronounced minima of the intensity also occur in the region of the fluorescent material. This is particularly advantageous in order to attenuate undesirable background signals and/or to achieve very highly selective excitation of the fluorescent material. In particular, in addition to the maxima, a minimum at an intermediate wavelength also occurs when amplifying at more than one wavelength owing to the formation of maxima of the field amplitude squares in the region of the surface of the fluorescence amplifier coating and/or in the fluorescent material.

In order to achieve a particularly good signal-to-background ratio, according to a refinement of the invention the interference layer system is designed so that the ratio of the amplitude squares of a first maximum of the amplitude square at a first wavelength to a neighboring minimum at a second wavelength is at least 5 to 1, preferably at least 10 to 1, and particularly preferably even at least 50 to 1. Therefore, inter alia, fluorescent light which would otherwise be excited by impurities at the wavelength of the minimum can be suppressed very effectively. The ratio of the intensities is in this case determined inter alia by the number of individual layers of the interference layer system.

Since the wavelength of the fluorescent light is furthermore comparatively close to the excitation wavelength, according to yet another preferred refinement of the invention the interference layer system is designed so that the intensity maximum of the amplitude square in the fluorescent material, or in the region close to or on the surface of the fluorescence amplifier coating, has a width at half maximum of at most 120 nanometers, preferably at most 100 nanometers.

There is a wide variety in the selection range of the dielectric materials for the high-index and low-index layers of the interference layer system. For applications in fluorescence measurement, however, they should be selected so that they do not fluorescence in the emission spectrum of the material to be analyzed.

As a rule, the designs preferably consist respectively of a high-index dielectric material and a low-index dielectric material. When the refractive index difference of the two low materials is greater, commensurately fewer layers will then be needed for the design of the fluorescence amplifier coating, for a given performance. It is preferable to use high-index oxides, for example $Al_2O_3$, $TiO_2$, $Ta_2O_5$, $Nb_2O_5$, $HfO_2$ or $ZrO_2$, or high-index nitrides and low-index oxides, for example $SiO_2$, or low-index nitrides.

However, layer designs with high-index layers of different high-index materials and/or low-index layers of different low-index materials may likewise be employed.

The choice of the substrate materials is very extensive, and will essentially be dictated by the intended use of the arrangement according to the invention. Owing to the reflective properties of the coating in the range of the excitation light, the latter does not enter the substrate. The substrate cannot therefore be excited. This greatly increases the range of possible substrate materials. For applications in fluorescence measurements, for which the arrangement is used as a sample carrier, the substrate is preferably a glass, a glass ceramic or a plastic. The arrangement according to the invention even makes it possible to use fluorescent substrates, since these no longer detrimentally affect the measurement.

The arrangement according to the invention allows highly accurate fluorescence detection, so that it can preferably used for analysis in biochip technology. In this case, the fluorescent material on the coating comprises an organic bonding layer and the fluorescent biological material to be studied.

The arrangement according to the invention is preferably suitable as a sample carrier, as a so-called microarray, with biological materials to be analyzed such as cells, nucleic acids, proteins, peptides and hydrocarbons in fluorescence spectroscopy.

The arrangement according to the invention is not restricted to these applications, however, but may be employed wherever it is desirable to amplify fluorescence. For instance, it is also possible to use it as an illuminating object. If the excitation light source lies inside the internally coated substrate, which is designed as an illuminating body, then the fluorescence amplifier coating and the substrate should be transmissive for the emission light. Such transparency in the emission spectral range is not possible with known metal/dielectric coatings.

When the arrangement according to the invention is used for the analysis of chemical and/or biological substances or other fluorescence analysis, or in cleaning procedures for recycling, it is preferable for it to be resistant to reagents during the analysis and/or the cleaning process. This applies in particular to the fluorescence amplifier coating. A typical example is the hybridization of DNA strands. It has been found that various layer systems are strongly attacked by the chemicals used in hybridization. A preferred refinement of the invention therefore relates to an arrangement having a fluorescence amplifier coating which is cleaning-resistant and/or unreactive.

In this context, it has been found that layer systems with layers that have been produced by plasma ion assisted vapor deposition are often chemically more resistance than layers produced by sputtering.

BRIEF DESCRIPTION OF THE SEVERAL VIEWS OF THE DRAWINGS

The invention will be described in more detail below with reference to exemplary embodiments. In respect of this.

DETAILED DESCRIPTION OF THE INVENTION

The exemplary embodiment relates to a microarray, for example for DNA analysis. The locally resolved photoluminescence is measured by using fluorescence spectroscopy through 2-dimensional scanning of the typically 2.5 cm*7.5 cm large slide with a laser scanner. The excitation is carried out, for example, with a laser beam of the excitation wavelength $\lambda_A = 532$ nm.

Figure 1:
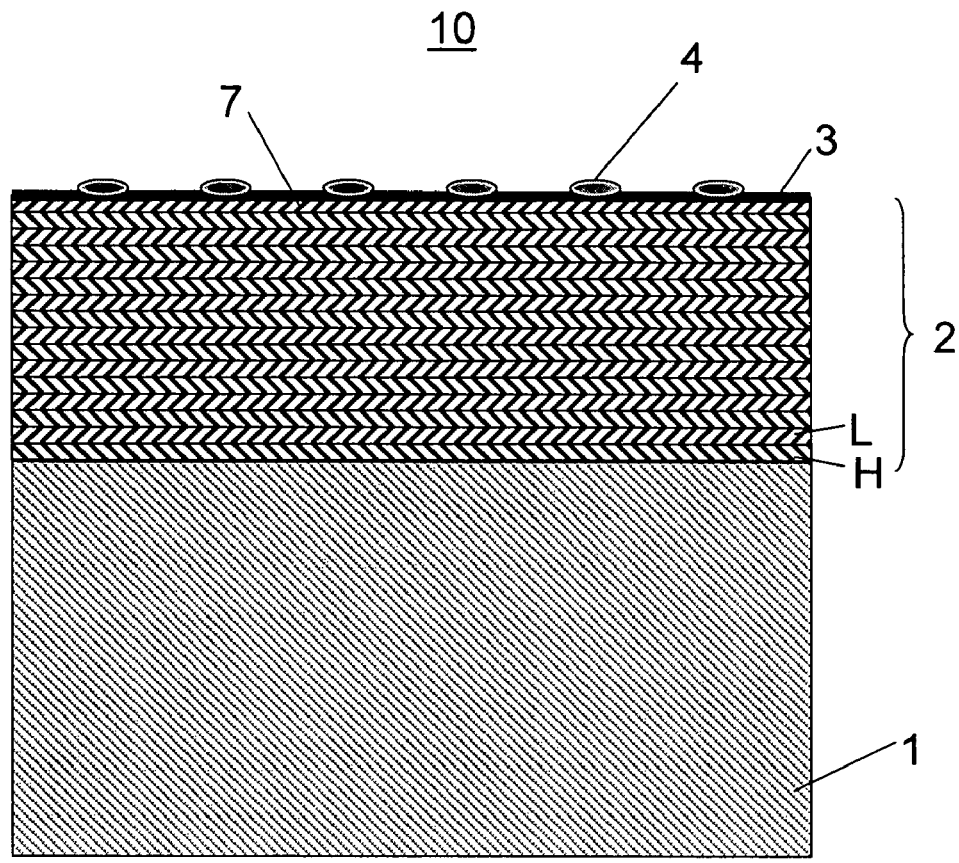
FIG. 1 shows the schematic representation of a microarray.

FIG. 1 shows a schematic structure, not true to scale, of a microarray denoted overall by 10 used for DNA analysis. The microarray 10 consists of a glass substrate (1), an interference layer system (2) which acts as a fluorescence amplifier coating, and fluorescent material which is applied on the surface 7 of the fluorescence amplifier coating, or the interference layer system 2, and which typically consists of an approximately 2 nm thick organic bonding layer (3) and, applied in the form of points, approximately 40 nm thick DNA half strand material with an attached fluorescent molecule (4), for example Cy3. A "DNA spot" which fluoresces after excitation in this case validates detection of successful DNA binding. The emitted light typically has an emission wavelength $\lambda_E$=580 nm. A high detection sensitivity is a prerequisite for such a successful analysis.

The detection sensitivity can be substantially increased by a special design of the interference layer system (2), which reflects the excitation light of the wavelength $\lambda_A$=532 and has a maximum of the electric field amplitude of the standing wave at the interface between the interference layer system (2) and the fluorescent material.

For example, this condition is satisfied by an interference layer system (2) as represented in FIG. 1 with the design $(HL)^8$, consisting of eight layer pairs respectively of a high-index layer (H) and a low-index layer (L), with the first high-index layer (H) lying on the substrate (1) and the last low-index layer (L) forming the interface with the fluorescent material.

The high-index layer (H) consists of $TiO_2$ with a refractive index of approximately 2.4, and the low-index layer (L) consists of $SiO_2$ with a refractive index of approximately 1.5. The optical thicknesses of the high-index and low-index layers (H, L) correspond to one fourth of the wavelength lambda of the excitation light with the wavelength $\lambda_A$=532 nm, which entails a layer thickness of 88.7 nm for the $SiO_2$ low-index layer (L) and a layer thickness of 55.4 nm for the $TiO_2$ high-index layer (H). The reflection of this design is more than 98% at $\lambda_A$=532 nm.

Through selection of the sequence and layer thicknesses of the high-index and low-index individual layers of the interference layer system 2, a phase relation of the excitation light is then obtained such that constructive interference between the incident and reflected excitation light occurs immediately on the surface or in the region of one half of the wavelength, preferably one fourth of the wavelength above the surface, wherever the fluorescent material is present in a vertical direction, and a maximum electric field strength is formed in the region of the applied fluorescing material.

With this interference layer system as the fluorescence amplifier coating, an increase in the fluorescence signal by the factor=10 was possible compared with uncoated substrates, and this was experimentally detected—see also FIGS. 5A, 5B, 6A, 6B discussed below.

The fluorescent material need not be a component of an arrangement according to the invention. Instead, an arrangement according to the invention may also (as represented by way of example in FIG. 1) be provided only subsequently with a layer having fluorescent material on the surface 7 of the interference layer system 2, for instance if the DNA half strand material with an attached fluorescent molecule 4 is not applied on a sample carrier configured according to the invention until the study, in order to form a microarray. In this variant of the invention as well, the interference layer system is designed so that the surface 7 of the fluorescence amplifier coating 2 is arranged in the region of the maximum of the electric field amplitude, in particular the square of this amplitude, of the standing wave formed with the excitation wavelength $\lambda_A$ which is formed during exposure to the excitation light. In particular, the intended layer thickness of the fluorescent material may also be taken into account in this case. For example, the surface 7 of the fluorescence amplifier coating may be arranged in the region of up to at most 50 nanometers below the maximum of the square of the field amplitude.

Figure 2A:
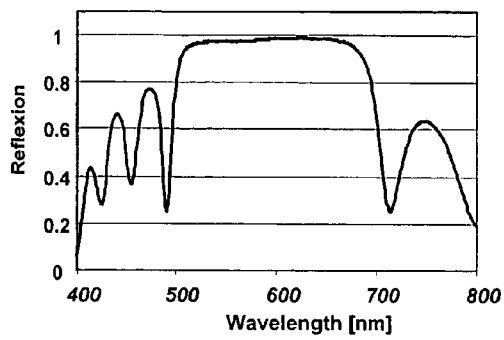
FIGS. 2A, 2B show the reflection spectrum and the square of the field strength at the surface of the fluorescence amplifier coating according to another exemplary embodiment of the invention.
Figure 2B:
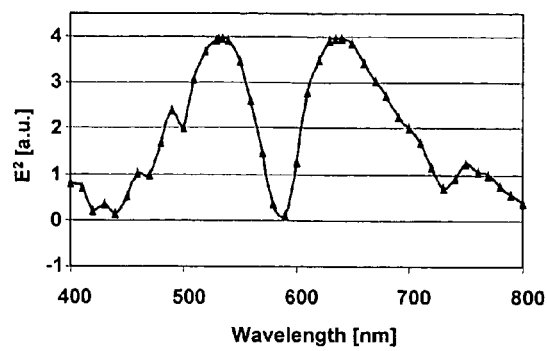

FIGS. 2A and 2B represent simulated profiles of the reflection and of the square of the amplitude, also referred to below as $E^2$, on the surface 7 of the fluorescence amplifier coating with the interference layer system 2, as a function of the wavelength of the excitation light. The layer structure of the interference layer system does not in this case correspond to the exemplary embodiment with a total of eight individual layers as explained with reference to FIG. 1. The layer system used here was specially designed so that it amplifies the fluorescence at the wavelengths of 532 nm and 635 nm typically used in practice.

Figure 3A:
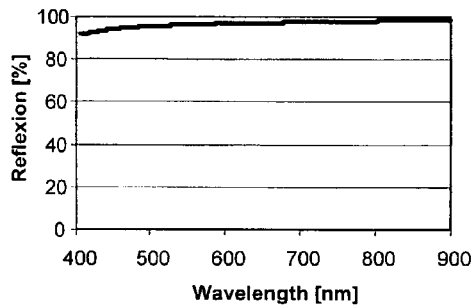
FIGS. 3A, 3B show for comparison the reflection spectrum and the square of the field strength at the surface of a glass/metal/$SiO_2$ layer system.
Figure 3B:
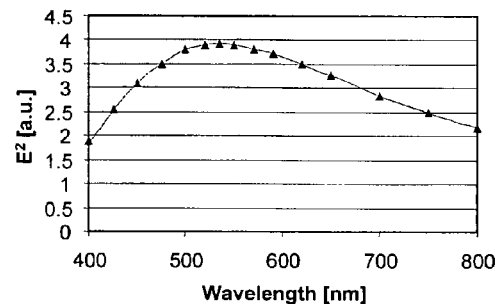

For comparison with this, FIGS. 3A and 3B show simulated profiles of the reflection and $E^2$ for a glass/metal/$SiO_2$ layer system. The structure of such a glass/metal/$SiO_2$ layer system corresponds in principle to an optical substrate as disclosed in WO 98/53304 A1. The layer thickness of the $SiO_2$ layer was assumed to be an odd multiple of a wavelength of 532 nanometers.

The metallically reflecting layer of a glass/metal/$SiO_2$ layer system reflects the light almost independently of the wavelength (FIG. 3A). Although an interference layer system 2 according to the invention also reflects the light over a wide wavelength range of from about 500 to 700 nanometers (FIG. 2A), very significant differences are nevertheless found in the spectral profile of $E^2$ on the surface of a substrate coated according to the invention (FIG. 2B) and a glass/metal/$SiO_2$ layer system (FIG. 3B).

In the case of a glass/metal/$SiO_2$ layer system, only a single broad maximum at 532 nanometers is found. In an arrangement according to the invention, conversely, there are two maximal in the visible spectral range. The number of maximum and their spectral positions can be adjusted to the respectively intended wavelengths by suitable selection of the layer thicknesses and/or the number of individual layers of the interference layer system, which represents a significant advantage over a metal/$SiO_2$ system. In the example shown in FIGS. 2A, 2B, the fluorescence amplifier coating is designed, in particular, so that the excitation light amplifies with a wavelength of 535 nanometers and 635 nanometers. Both wavelengths are commonly used for fluorescence analysis on DNA molecules. An arrangement according to the invention can therefore be tailored very easily for a plurality of accurately definable wavelengths of the excitation light. The maximum of the amplitude square of the excitation light in the fluorescent material, or in the region near to or on the surface of the fluorescence amplifier coating, furthermore has a width at half maximum of less than 100 nanometers in the example shown in FIG. 2B, and are therefore substantially narrower than the maximum which occurs with a glass/metal/$SiO_2$ layer system.

FIGS. 2A, 2B, and 3A, 3B also make it clear that in an arrangement according to the invention, with fluorescent material which is or can be applied, the metallically reflecting layer is not merely replaced by a dielectric mirror. Although the interference layer system appears purely visually like a mirror, just as important as the reflecting property of the interference layer system 2 is the phase relation of the incident and emerging radiation on the surface, or in the region of the fluorescent material. It is only the phase relation which establishes the spectral position of the maxima and minima of the electric field strength and, for a design which spectrally reflects broadly, determines the exact (excitation) wavelengths at which only the fluorescence is amplified or reduced.

The interference layer system is furthermore designed so that the phase relation of the excitation light remains constant along the surface in the region of the fluorescent material. This prevents intensity minima from occurring in addition to intensity maxima along the surface in the region of the fluorescent material. Laterally with respect to each position of the surface where fluorescent material is arranged, therefore, essentially the same amplification or the same spectral profile of $E^2$ as shown by way of example in FIG. 2B is obtained.

Another difference of an arrangement according to the invention from a metallically reflecting layer with a SiO$_2$ layer deposited on top is that besides the maxima at 635 nanometers and 535 nanometers, there is also a significant minimum of the intensity lying between the maxima. This has the advantage that less undesirable background fluorescence is excited by broadband excitation, in particular with commonly used white light interferometers. For example, if there are surface impurities which emit fluorescent light with a wavelength of 600 nm when excited at 580 m—this is possible inter alia with organic molecules—then this undesired extraneous fluorescence would be amplified significantly more with a glass/metal/SiO$_2$ structure having a characteristic corresponding to FIGS. 3A, 3B than by a dielectric structure according to the invention.

This behavior follows directly from the pronounced E$^2$ distribution on the surface of the interference layer system 2 or in the fluorescent material arranged on it. In order to minimize such background signals, it is then preferable for the ratio of the amplitude square of a maximum of the amplitude square at a first wavelength to a neighboring minimum at a second wavelength to be at least 5 to 1, preferably at least 10 to 1, and particularly preferably even at least 50 to 1. In the example shown in FIG. 2B, this ratio is more than 50 to 1 for each of the maximum.

Figure 4A:
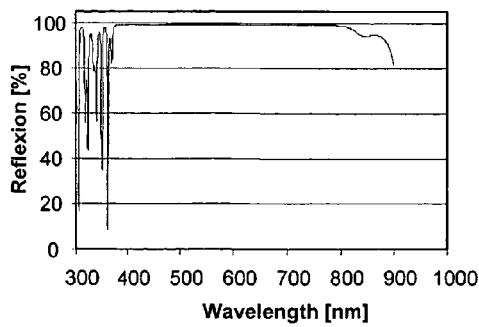
FIGS. 4A and 4B show the reflection spectrum and the square of the field strength at the surface of the fluorescence amplifier coating according to an exemplary embodiment having 52 individual layers in the layer stack of the fluorescence amplifier coating.
Figure 4B:
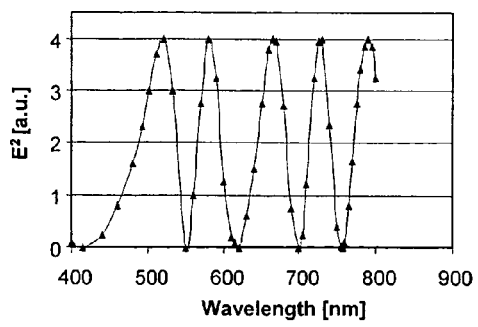

FIGS. 4A and 4B show the characteristic of another exemplary embodiment of the invention. FIG. 4A shows the reflection spectrum and FIG. 4B shows the square of the field strength at the surface of the fluorescence amplifier coating. In this exemplary embodiment, the interference layer system comprises 52 layers of alternating high-index and low-index materials. In this exemplary embodiment, it is found that this interference layer system essentially has a uniformly high reflection over the entire visible spectral range. Owing to the larger number of layers, in particular, there are only in fact 5 maxima of the square of the field strength at the surface of the interference layer system 2 in the range of the visible spectrum.

Figure 5A:
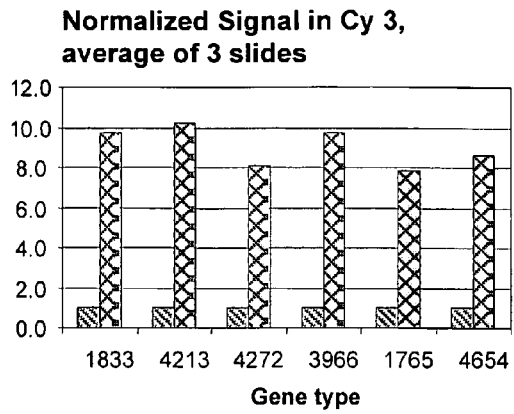
FIGS. 5A and 5B show a comparison of the signal strength of fluorescence signals in different fluorescence channels using sample carriers configured conventionally and according to the invention for a plurality of genes.
Figure 5B:
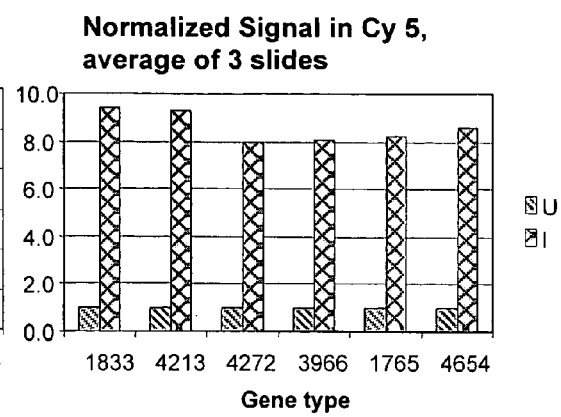
Figure 6A:
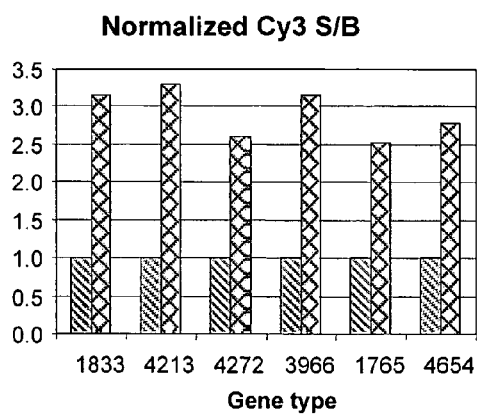
FIGS. 6A and 6B show a comparison of the signal-to-background ratio for the signals shown in FIGS. 5A and 5B, FIGS. 7A and 7B show ratios of the signal levels of fluorescence signals on Cy5 and Cy3 molecules, measured on uncoated sample carriers and sample carriers according to the invention, the ratios in FIG. 7B being shown normalized to the signal ratio of uncoated sample carriers.
Figure 6B:
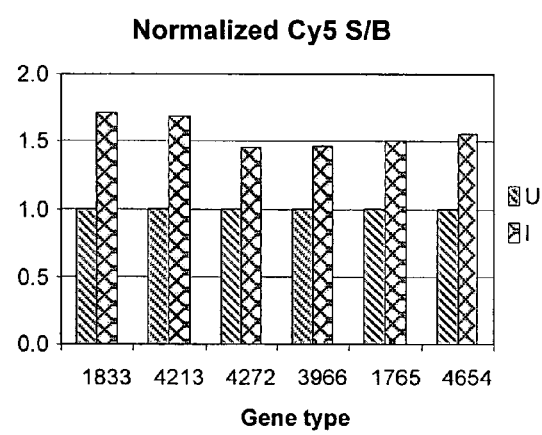

FIGS. 5A, 5B, 6A, 6B shows measurement results for the fluorescence signals of genes in the form of bar charts. In this case, the bars denoted by "U" respectively denote the measurement values obtained on uncoated conventional sample carriers and the bars denoted by "I" denote the measurement values obtained on sample carriers configured according to the invention. In each of the bar charts, the measurement values are represented for six different gene types. FIG. 5A shows the measurements on the fluorescence molecule Cy3 at a wavelength of 535 nanometers and FIG. 5B shows the measurements on the fluorescence molecule Cy5 at a wavelength of 635 nanometers for the excitation light. FIGS. 6A and 6B represent the signal-to-background ratio of the signals shown in FIGS. 5A and 5B, respectively. As can be seen from FIGS. 5A and 5B, the signals of sample carriers according to the invention with an interference layer system 2 are respectively higher at least by a factor of 8 than those of conventional sample carriers.

In particular, the signal/background ratio is also substantially better than in conventional sample carriers, as represented with the aid of FIGS. 6A and 6B. For the fluorescence at 635 nanometer excitation (FIG. 6B), the signal-to-background ratio is greater at least by about a factor of 1.5, and even at least by a factor of 2.5 at 535 nanometers, compared with uncoated sample carriers. If the background signals are subtracted from the signals shown in FIGS. 5A and 5B, then an amplification of the measurement signal is obtained which is respectively higher at least by a factor of 10 with sample carriers according to the invention.

Figure 7A:
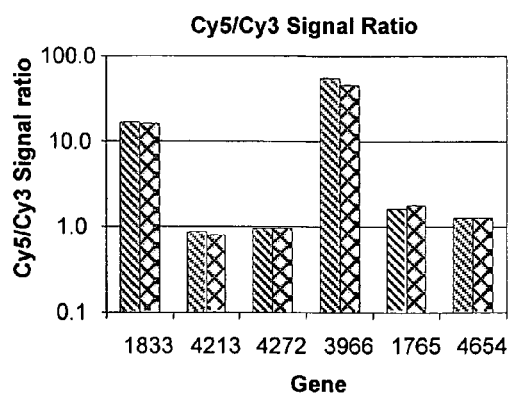
Figure 7B:
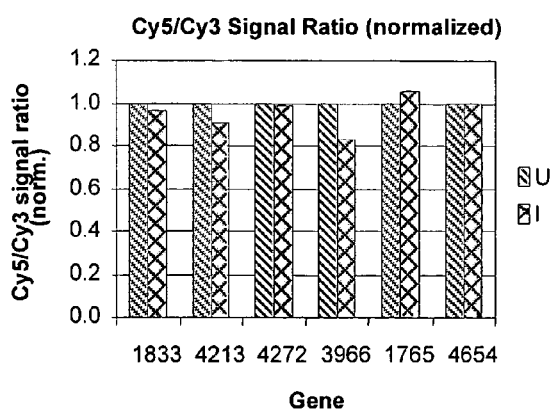

FIGS. 7A and 7B show ratios of the signal levels of fluorescence signals on Cy5 and Cy3 molecules, measured on uncoated sample carriers and sample carriers according to the invention, the ratios in FIG. 7B being shown normalized to the signal ratio of uncoated sample carriers. For the excitation, the ratio of the fluorescence with excitation at 535 nm (Cy3 molecules) to the excitation at 635 nm (Cy5 molecules) is important. This ratio shown in FIGS. 7A and 7B should as far as possible remain unchanged. Although the ratio fluctuates greatly from gene to gene (FIG. 7A), it nevertheless does so to the same extent in sample carriers according to the invention and uncoated sample carriers. Even when the ratios are normalized to the signal ratios found on uncoated sample carriers, only minor deviations are found.

Figure 8A:
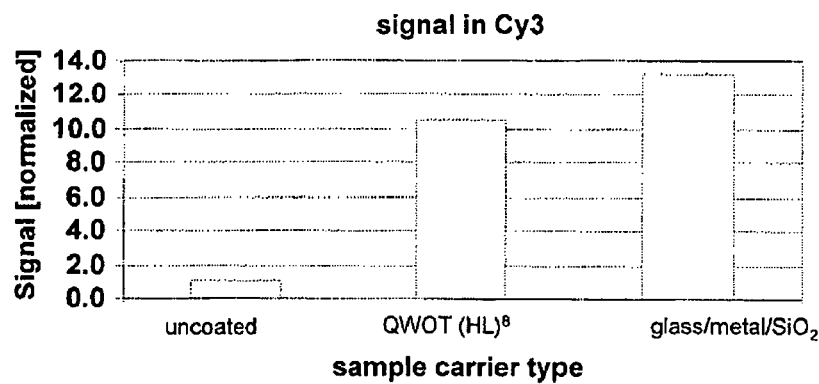
FIGS. 8A to 8C show comparisons of the average values of fluorescence signals, background signals and the signal-to-background ratio for an uncoated sample carrier, a sample carrier according to the invention and a sample carrier with a glass/metal/$SiO_2$ layer system.
Figure 8B:
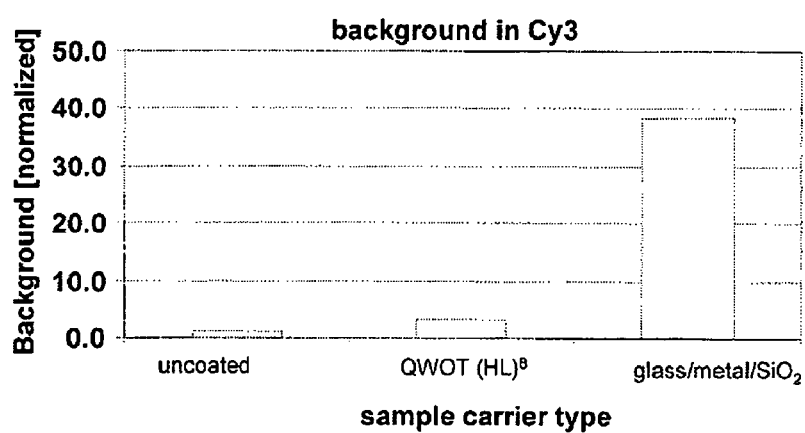
Figure 8C:
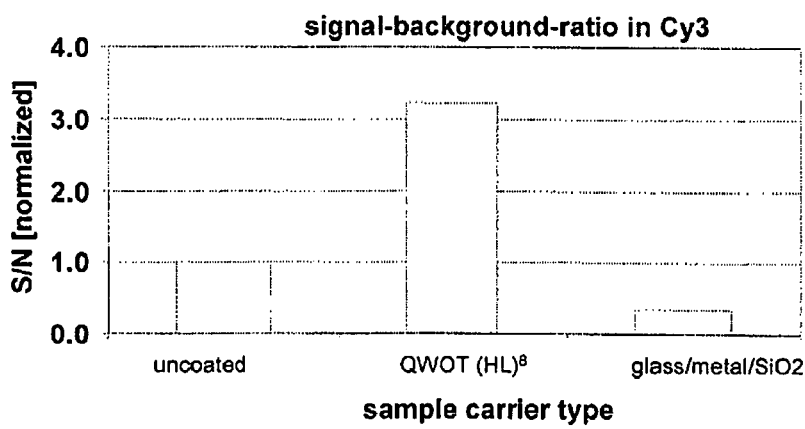

FIGS. 8A to 8C show comparisons of the measurement values of fluorescence signals (FIG. 8A), background signals (FIG. 8B) and the signal-to-background ratio (FIG. 8C) for an uncoated sample carrier (respectively on the left in the bar charts), a sample carrier according to the invention (QWOT (HL)$^8$) and a sample carrier with a glass/metal/SiO$_2$ layer system (respectively on the right in the charts). The fluorescence of a Cy3 fluorescent dye when excited by light with a wavelength of 535 nanometers was in this case measured. The sample carrier according to the invention corresponds to a microarray with an eight-layered interference system, as represented in FIG. 1. With the aid of the measurement values plotted in FIGS. 8A to 8C, it can be seen that although a sample carrier with a glass substrate, metallically reflecting layer and an SiO$_2$ spacer layer delivers the highest signals (FIG. 8A), it nevertheless delivers more background signal (FIG. 8B) and therefore gives an inferior signal-to-noise ratio than a microarray 10 according to the invention. Even the uncoated support shows a better signal-to-noise ratio.

When an arrangement according to the invention is used as a sample carrier or microarray, it is found that an interference layer system has very highly advantageous optical properties compared with previously known arrangements. The individual layers are very thin, however, and may sometimes be degraded by cleaning procedures. Nevertheless, it is possible to produce cleaning-resistant and/or unreactive fluorescence amplifier coatings by a particular deposition method, plasma ion assisted vapor deposition.

Figures 9A, 9B:
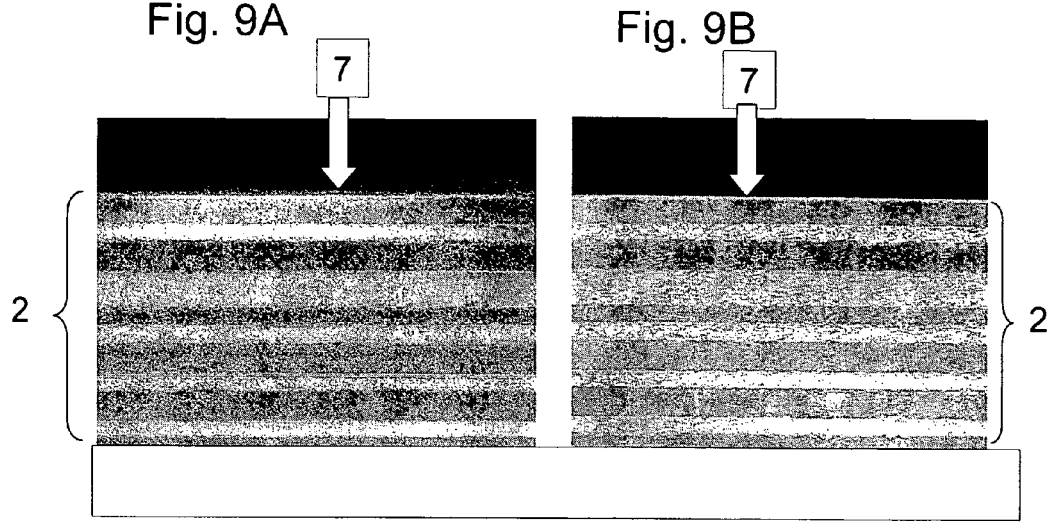
FIGS. 9A and 9B show scanning electron images of an interference layer system according to a refinement of the invention, with layers applied by plasma ion assisted vapor deposition, before and after cleaning.

FIGS. 9A and 9B show scanning electron images of an interference layer system 2 according to a refinement of the invention [lacuna] layers deposited in this way before (FIG. 9A) and after (FIG. 9B) a cleaning procedure, as is typically carried out for sample carriers. Even after the cleaning, no substantial changes of the layer structure are found.

Figures 10A, 10B:
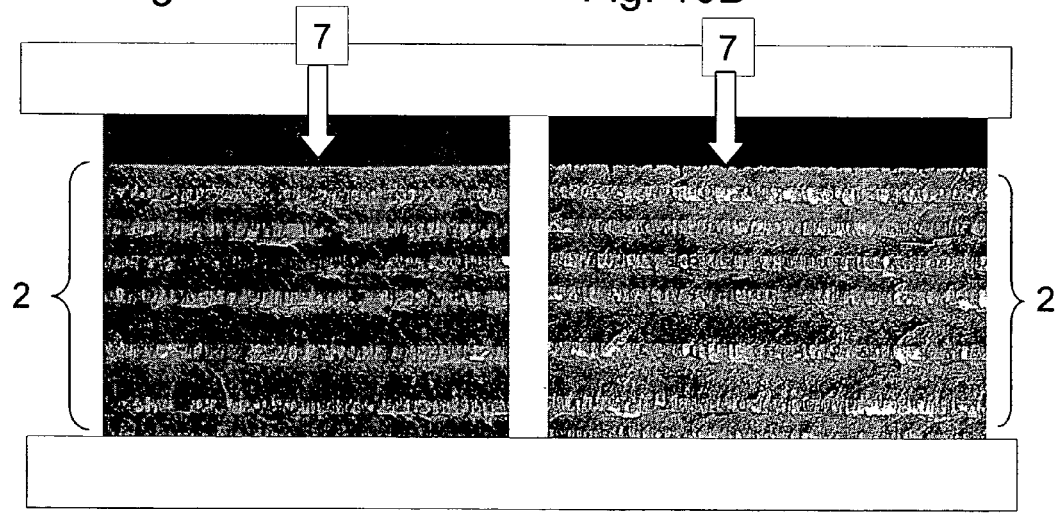
FIGS. 10A and 10B show for comparison scanning electron images of an interference layer system produced by vapor coating without plasma ion assisted deposition, before and after cleaning.

FIGS. 10A and 10B represent for comparison scanning electron images of an interference layer system produced by vapor coating without plasma ion assisted deposition, before and after such cleaning. There are found to be trenches after the cleaning, some of which are marked by arrows in FIG. 10B. After repeated cleaning cycles, strong degradation of the layer system can therefore take place. Such defects are also found with sputtered layers. Degradation of sputtered layers is even encountered when a hybridization reaction is carried out on the sample carrier. Detachment of the top layer may then even take place.

Besides deposition of the layers by means of plasma ion assisted vapor deposition, other measures are also possible for obtaining a fluorescence amplifier coating which is resistant to reagents during analysis and/or a cleaning process. For example, a suitable barrier coating may be applied on the interference layer system, or may even form a part of the interference layer system. For example, the top layer of the interference layer system may be a unreactive plastic layer, in order to obtain a fluorescence amplifier coating which is resistant to reagents during analysis and/or a cleaning process.

Figure 11:
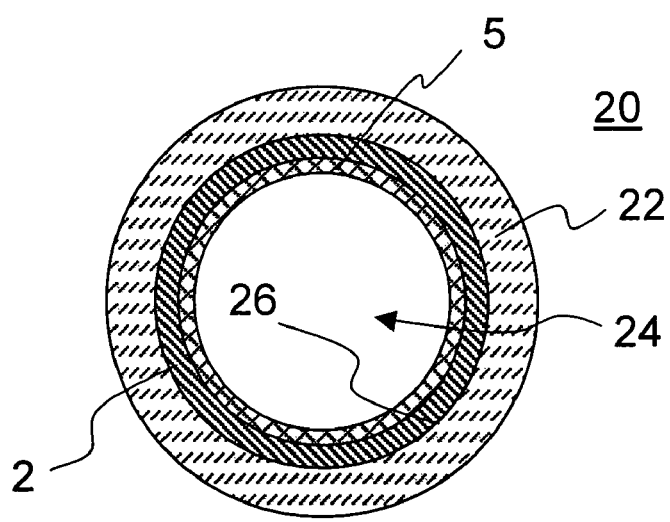
FIG. 11 shows another embodiment of the invention in the form of a fluorescent tube.

FIG. 11 represents another embodiment of the invention. FIG. 11 shows in cross section a fluorescent tube 20 with a glass tube 22 as the substrate. The interior 24 of the glass tube 22 in this case forms the gas discharge space. On the inner wall 24 of the glass tube, a fluorescence amplifier coating is again applied which has an interference layer system 2, the individual high-index and low-index layers of which, here arranged concentrically with the cylinder axis of the glass tube 22, are not represented for the sake of clarity. A fluorescent coating 5 is applied on the interference layer system 2. Here again, as in the example represented in FIG. 1, the interference layer system 2 and the coating 5 are designed so that the former reflects at least the excitation light and the fluorescent material on the coating is arranged in the region of the maximum of the electric field amplitude, in particular the maximum of $E^2$ of the standing wave with the excitation wavelength $\lambda_A$ which is formed during exposure to the excitation light. The layer system 2 is generally to be configured here in terms of its layer thicknesses differently than in the example shown in FIG. 1, since the plasma of a gas discharge tube typically has one or more intense lines in the ultraviolet spectral range. If a plurality of lines are present then, as explained with reference to FIG. 2B and FIG. 4B, the intensity can be amplified in a controlled way inside the fluorescent layer 5. So that the fluorescent light generated in the layer 5 can emerge, in this exemplary embodiment the interference layer system 2 is furthermore designed as an optical filter which transmits light in the range of the emission wavelength $\lambda_E$.

It is clear to the person skilled in the art that the invention is not restricted to the embodiments described above but may be varied in many ways. In particular, the features of the individual exemplary embodiments may also be combined with one another. The application of the invention is also explicitly not restricted to fluorescence spectroscopy for the analysis of microarrays, but may likewise be used wherever fluorescence of thin layers is intended to be measured, for example in the fields of quality control.

The invention claimed is:

1. An arrangement for fluorescence enhancement, comprising:
   a substrate;
   a fluorescence enhancing coating applied on the substrate; and
   a fluorescencable material on the fluorescence enhancing coating, wherein the fluorescencable material, when irradiated with an excitation light of an excitation wavelength $\lambda_A$, emits light in an emission wavelength $\lambda_E$,
   wherein the fluorescence-enhancing coating has a light reflecting interference layer system comprising high and low refractive index dielectric layers so that an enhanced electric field amplitude of the excitation light is achieved in the region of the fluorescencable material by a constructive superposition of the electric field amplitudes of the incident and the reflected excitation light, and
   wherein the interference layer system is effective to amplify excitation by reflection of light having a first wavelength and a discrete second wavelength,
   wherein interference of the first wavelength results in a doubling of the electric field amplitude of the first wavelength and in an excitation maximum in the region of the fluorescencable material,
   wherein interference of the discrete second wavelength results in an extinction of the electric field amplitude of the second wavelength and in an excitation minimum in the region of the fluorescencable material, and
   wherein the excitation maximum has a ratio to the excitation minimum of at least 5 to 1.

2. The arrangement as claimed in claim 1, the reflecting interference layer system of the fluorescence-enhancing coating is designed so that a maximum of an electric field amplitude of a standing wave is achieved in the region of the fluorescencable material by a constructive superposition of the electric field amplitudes of the incident and the reflected excitation light.

3. The arrangement as claimed claim 2, wherein the incident and reflected excitation light has a phase relation that remains constant along the surface.

4. The arrangement as claimed in claim 2, wherein the surface is in a region of up to about 50 nanometers below a maximum of a square of the electric field amplitude.

5. The arrangement as claimed in claim 2, wherein the surface is arranged in the region of a square of the electric field amplitude.

6. The arrangement as claimed in claim 1, wherein the fluorescence-enhancing coating comprises an interference layer system having a plurality of high-index dielectric layers and a plurality of low-index dielectric layers that reflect at least the excitation light.

7. The arrangement as claimed in claim 6, wherein the interference layer system forms a phase relation of the excitation light with a constructive interference between an incident excitation light and a reflected excitation light immediately on a surface of the fluorescence-enhancing coating, and wherein the interference layer system forms a maximum electric field amplitude in a region of the fluorescencable material.

8. The arrangement as claimed in claim 6, wherein the plurality of high-index dielectric layers and the plurality of low-index dielectric layers alternate, and wherein each of the plurality of high-index dielectric layers and each of the plurality of low index dielectric layers has an optical layer thickness that corresponds to one fourth of the excitation wavelength.

9. The arrangement as claimed in claim 6, wherein the plurality of high-index dielectric layers and the plurality of low-index dielectric layers are between the substrate and the fluorescencable material, and wherein each of the plurality of high-index dielectric layers is adjacent to at least one of the plurality of low-index dielectric layers forming a plurality of pairs.

10. The arrangement as claimed in claim 9, wherein the substrate is adjacent to one of the plurality of low-index dielectric layers and the fluorescence material is adjacent to one of the plurality of high-index dielectric layers.

11. The arrangement as claimed in claim 6, wherein the interference layer system is an optical filter that reflects light in a range of the excitation wavelength, wherein the interference layer system has a bandwidth greater than or equal to the excitation wavelength minus 20 nanometers but less than or equal to the excitation wavelength plus 20 nanometers, and wherein the interference layer system has a reflectivity in a band range of more than 50%.

12. The arrangement as claimed in claim 6, wherein the interference layer system is an optical filter that transmits light in a range of the emission wavelength.

13. The arrangement as claimed in claim 6, wherein the interference layer system reflects light of a plurality of different excitation wavelengths.

14. The arrangement as claimed in claim 6, wherein each of the plurality of high-index dielectric layers is selected from a group consisting of a high-index oxide and a high-index nitride.

15. The arrangement as claimed in claim 6, wherein each of the plurality low-index dielectric layers is selected from a group consisting of a low-index oxide and a low-index nitride.

16. The arrangement as claimed in claim 6, wherein the fluorescencable material comprises an organic bonding layer and a fluorescent biological material.

17. The arrangement as claimed in claim 16, wherein the organic bonding layer is selected from a group consisting of aminosilanes, aminopropyl silanes, epoxy silanes and hydrogel layers.

18. The arrangement as claimed in claim 16, wherein the fluorescent biological material is selected from a group consisting of cells, nucleic acids, proteins, peptides, and hydrocarbons.

19. The arrangement as claimed in claim 16, wherein the fluorescent biological material comprises Cy3 molecules or Cy5 molecules.

20. The arrangement as claimed in claim 6, wherein the plurality of high-index layers and the plurality of low-index layers are produced by plasma ion assisted vapor deposition.

21. The arrangement as claimed in claim 6, wherein the interference layer system is effective to result in an enhanced fluorescence excitation with an intensity maximum having a full width at a half maximum of at most 120 nanometers.

22. The arrangement as claimed in claim 6, wherein the interference layer system forms a phase relation of the excitation light with a constructive interference between an incident excitation light and a reflected excitation light in a region of one half of the excitation wavelength, and wherein the interference layer system forms a maximum electric field in a region of the fluorescing material.

23. The arrangement as claimed in claim 6, wherein the interference layer system forms a phase relation of the excitation light with a constructive interference between an incident excitation light and a reflected excitation light in a region of one fourth of the excitation wavelength, and wherein said interference layer system forms a maximum electric field in the region.

24. The arrangement as claimed in claim 6, wherein the plurality of high-index dielectric layers and the plurality of low-index dielectric layers are between the substrate and the fluorescencable material, wherein each of the plurality of high-index dielectric layers is adjacent to at least one of the plurality of low-index dielectric layers forming a plurality of pairs, and wherein the plurality of pairs comprise four pairs.

25. The arrangement as claimed in claim 6, wherein the plurality of high-index dielectric layers and the plurality of low-index dielectric layers are between the substrate and the fluorescencable material, wherein each of the plurality of high-index dielectric layers is adjacent to at least one of the plurality of low-index dielectric layers forming a plurality of pairs, and wherein the plurality of pairs comprise eight pairs.

26. The arrangement as claimed in claim 6, wherein the interference layer system is an optical filter that reflects light in a range of the excitation wavelength, wherein the interference layer is effective in a bandwidth greater than or equal to the excitation wavelength minus 10 nanometers but less than or equal to the excitation wavelength plus 10 nanometers, and wherein the interference layer has a reflectivity in a band range of more than 50%.

27. The arrangement as claimed in claim 6, wherein the interference layer system is an optical filter that reflects light in a range of the excitation wavelength, wherein the interference layer is effective in a bandwidth greater than or equal to the excitation wavelength minus 20 nanometers but less than or equal to the excitation wavelength plus 20 nanometers, and wherein the interference layer has a reflectivity in a band range of more than 80%.

28. The arrangement as claimed in claim 6, wherein the excitation maximum has a ratio to the excitation minimum of at least 10 to 1.

29. The arrangement as claimed in claim 6, wherein each of the plurality of high-index dielectric layers is selected from a group consisting of a $Al_2O_3$, a $TiO_2$, a $Ta_2O_5$, a $Nb_2O_5$, a $HfO_2$, and a $ZrO_2$.

30. The arrangement as claimed in claim 6, wherein each of the plurality of low-index dielectric layers is $SiO_2$.

31. The arrangement as claimed in claim 6, wherein the interference layer system is effective to result in an enhanced fluorescence excitation with an intensity maximum having a full width at a half maximum of at most 120 nanometers.

32. The arrangement as claimed in claim 1, wherein the fluorescencable material has an optical thickness of less than one fourth of the excitation wavelength.

33. The arrangement as claimed in claim 1, wherein the excitation light is amplified with an excitation wavelength of about 535 nanometers and/or about 635 nanometers in a region of the fluorescencable material.

34. The arrangement as claimed in claim 1, wherein the substrate is selected from a group consisting of a glass, a glass ceramic, and a plastic.

35. The arrangement as claimed in claim 1, wherein the arrangement is used as a microarray.

36. The arrangement as claimed in claim 1, wherein the arrangement is used as a sample carrier in a fluorescence detection system.

37. The arrangement as claimed in claim 1, wherein the arrangement is used as an illuminating object.

38. The arrangement as claimed in claim 1, wherein the arrangement is used as a fluorescent tube.

39. The arrangement as claimed in claim 1, wherein the arrangement is a sample carrier with fluorescence amplification.

40. The arrangement as claimed in claim 1, wherein the fluorescence-enhancing coating is resistant to reagents during analysis and/or a cleaning process.

41. An arrangement for fluorescence reinforcement, comprising:
   a substrate;
   a fluorescence-strengthening coating applied on the substrate, the fluorescence-strengthening coating having a light reflecting interference layer system of alternating high refractive index dielectric layers and low refractive index dielectric layers; and
   a fluorescencable material on the fluorescence-strengthening coating, the fluorescencable material having a thickness smaller than 50 nanometers, wherein the fluorescencable material, when irradiated with light of an excitation wavelength $\lambda_A$, emits light in an emission wavelength $\lambda_E$, wherein each of the high refractive index dielectric layers and low refractive index dielectric layers has an optical layer thickness that corresponds to one fourth of the excitation wavelength $\lambda_A$, and
   wherein the interference layer system is effective to amplify excitation light by reflection of light having a first wavelength and a discrete second wavelength, wherein interference of the first wavelength results in a doubling of the electric field amplitude of the first wavelength and in an excitation maximum in the region of the fluorescenable material, wherein interference of the discrete second wavelength results in an extinction of the electric field amplitude of the second wavelength and in a excitation minimum in the region of the fluorescencable material, and wherein the excitation maximum has a ratio to the excitation minimum of at least 5 to 1.

42. An arrangement for fluorescence enhancement, comprising:

a substrate;

a fluorescence-enhancing coating applied on the substrate, the fluorescence-strengthening coating having a light reflecting interference layer system with a plurality of high-index dielectric layers and a plurality of low-index dielectric layers that reflect at least the excitation light; and a fluorescencable material on the fluorescence-strengthening coating, wherein the fluorescencable material, when irradiated with an excitation light of an excitation wavelength $\lambda_A$, emits light in an emission wavelength $\lambda_E$, wherein the light reflecting interference layer system reflects light in a range of the excitation wavelength, wherein the light reflecting interference layer system has a bandwidth greater than or equal to the excitation wavelength minus 20 nanometers but less than or equal to the excitation wavelength plus 20 nanometers, and wherein the light reflecting interference layer system has a reflectivity in a band range of more than 50%, wherein the light reflecting interference layer system is effective to amplify excitation by reflection of light having a first wavelength and a discrete second wavelength, wherein interference of the first wavelength results in doubling of the electric field amplitude of the first wavelength and in an excitation maximum in the region of the fluorescencable material, wherein interference of the discrete second wavelength results in an extinction of the electric field of the second wavelength and in an excitation minimum in the region of the fluorescencable material, and wherein the excitation maximum has a ratio to the excitation minimum of at least 5 to 1.

43. An arrangement for fluorescence enhancement, comprising:

a substrate;

a fluorescence-enhancing coating applied on the substrate, the fluorescence-strengthening coating having a light reflecting interference layer system with a plurality of high-index dielectric layers and a plurality of low-index dielectric layers that reflect at least the excitation light; and a fluorescencable material on the fluorescence-strengthening coating, wherein the fluorescencable material, when irradiated with an excitation light of an excitation wavelength $\lambda_A$, emits light in an emission wavelength $\lambda_E$, wherein the light reflecting interference layer system reflects light in a range of the excitation wavelength, wherein the light reflecting interference layer system is effective to amplify excitation by reflection of light having a first wavelength and a discrete second wavelength, wherein interference of the first wavelength results in a doubling of the electric field amplitude of the first wavelength and in an excitation maximum in the region of the fluorescencable material, wherein interference of the discrete second wavelength results in an extinction of the electric field of the second wavelength an in an excitation minimum in the region of the fluorescencable material, and wherein the excitation maximum has a ratio to the excitation minimum of at least 5 to 1.

\* \* \* \* \*